US012345716B2

(12) United States Patent
Roennau et al.

(10) Patent No.: US 12,345,716 B2
(45) Date of Patent: Jul. 1, 2025

(54) METHOD FOR MANUFACTURING A TUMOR VACCINE

(71) Applicant: VCC Medical Deutschland GmbH, Ludwigshafen (DE)

(72) Inventors: Helge Roennau, Ludwigshafen (DE); Stephan Kiessig, Ludwigshafen (DE)

(73) Assignee: VCC Medical Deutschland GmbH, Ludwigshafen (DE)

( * ) Notice: Subject to any disclaimer, the term of this patent is extended or adjusted under 35 U.S.C. 154(b) by 446 days.

(21) Appl. No.: 16/628,058

(22) PCT Filed: Jun. 18, 2018

(86) PCT No.: PCT/EP2018/066119
§ 371 (c)(1),
(2) Date: Jan. 2, 2020

(87) PCT Pub. No.: WO2019/007665
PCT Pub. Date: Jan. 10, 2019

(65) Prior Publication Data
US 2021/0364528 A1 Nov. 25, 2021

(30) Foreign Application Priority Data
Jul. 5, 2017 (EP) ..................................... 17179714

(51) Int. Cl.
*G01N 33/68* (2006.01)
*A61K 39/00* (2006.01)
*A61P 35/00* (2006.01)
*G01N 33/574* (2006.01)

(52) U.S. Cl.
CPC ...... *G01N 33/6854* (2013.01); *A61K 39/0011* (2013.01); *A61P 35/00* (2018.01); *G01N 33/57438* (2013.01); *A61K 2039/55505* (2013.01); *A61K 2039/55516* (2013.01); *G01N 2500/00* (2013.01)

(58) Field of Classification Search
CPC ........................... G01N 33/564; G01N 33/566
See application file for complete search history.

(56) References Cited

U.S. PATENT DOCUMENTS

2003/0129206 A1    7/2003  Ulbrich et al.
2007/0134275 A1    6/2007  Ulbrich et al.

FOREIGN PATENT DOCUMENTS

| EP | 1305041 A1 | 5/2003 | |
|----|-----------|--------|---|
| EP | 1974742 A1 | 10/2008 | |
| WO | WO-9958978 A2 * | 11/1999 | ......... C07K 14/4748 |
| WO | WO-2008109030 A2 * | 9/2008 | ....... G01N 33/57434 |
| WO | WO-2012112013 A2 * | 8/2012 | .............. C07K 16/18 |

OTHER PUBLICATIONS

Han et al (Journal of Translational Medicine, 2017, vol. 15, No. 64, 13 pages). (Year: 2017).*
Hoene et al.(Journal of Leukocyte Biology, 2006, vol. 80, pp. 1328-1336). (Year: 2006).*
Schuster et al ("Immunotherapy of Renal Cell Carcinoma-From Antigen Identification to Patient Treatment", In: Emerging Research and Treatments in Renal Cell Carcinoma, IntechOpen, 2012) (Year: 2012).*
Van Poppel et al (European Urology, 2009, vol. 55, pp., 1333-1344) (Year: 2009).*
Bukhari et al (Molecular Biosystems, 2015, vol. 11, pp. 159-169) (Year: 2015).*
International Search Report of PCT/EP2018/066119, mailed Jul. 30, 2018.
International Preliminary Report on Patentability of PCT/EP2018/066119, mailed Oct. 2, 2019.
Wittke et al. : "Rationales for a multi-epitope approach in autologous rean cell cancer tumor vaccine", Journal of Vaccines & Vaccination, 2016, ISSN:2157-7560 JVV, vol. 7, issue 4, pp. 1-5.
Jocham et al.: "Adjuvant autologous renal tumour cell vaccine and risk of tumour progression in patients with renal-cell carcinoma after radical nephrectomy: phase III, randomised controlled trial", The Lancet, vol. 363, Feb. 21, 2004, pp. 594-599.
Steffan Wittke et al: "Tumor heterogeneity as a rationale for a multi-epi tope approach in an autologous renal cell cancer tumor vaccine", Oncotargets and Therapy, Jan. 1, 2016 (Jan. 1, 2016), p. 523, XP055426650.
Matthias May et al: "Ten-year survival analysis for renal carcinoma patients treated with an autologous tumour lysate vaccine in an adjuvant setting", Cancer Immunology, Immunotherapy, Springer, Berlin, Germany, vol. 59, No. 5, Oct. 30, 2009, pp. 687-695, XP019800190.
Shaun McNulty et al: "Heat-shock proteins as dendritic cell-targeting vaccines—getting warmer", Immunology, vol. 139, No. 4, Jul. 2, 2013, pp. 407-415, XP055427131.
Sujin Lee et al: Recent advances of vaccine adjuvants for infectious diseases, Immune Network, vol. 15, No. 2, Jan. 1, 2015, p. 51, XP055427148.

(Continued)

*Primary Examiner* — Karen A. Canella
(74) *Attorney, Agent, or Firm* — Collard & Roe, P.C.

(57) ABSTRACT

A method of identifying an effective composition of antigens for a tumor vaccine includes determination of antibodies produced by at least 10 patients after vaccination with an autologous vaccine obtained by gathering tumor material from the patients, separating the tumor cells from accompanying tissue, inactivating the tumor cells and providing them in a form suitable for administration as autologous vaccine, application of the autologous vaccine to the patients, isolation and determination of the antibodies produced by the patients' immune response that have been found to be shared by at least 80% of the patients, and identifying the antigens corresponding to the determined antibodies. A method of manufacturing a tumor vaccine is performed from the identified antigens and danger signals, and a tumor vaccine is obtained thereby.

12 Claims, No Drawings

Specification includes a Sequence Listing.

(56) References Cited

OTHER PUBLICATIONS

X.Y. Wang et al: "Superior antitumor response induced by large stress protein chaperoned protein antigen compared with peptide antigen", The Journal of Immunology, vol. 184, No. 11, May 3, 2010, pp. 6309-6319, XP055427455.

* cited by examiner

METHOD FOR MANUFACTURING A TUMOR VACCINE

CROSS REFERENCE TO RELATED APPLICATIONS

This application is the National Stage of PCT/EP2018/066119 filed on Jun. 18, 2018, which claims priority under 35 U.S.C. § 119 of European Application No. 17179714.5 filed on Jul. 5, 2017, the disclosures of which are incorporated by reference. The international application under PCT article 21 (2) was published in English.

REFERENCE TO AN ELECTRONIC SEQUENCE LISTING

The contents of the electronic sequence listing (sequence-listing.txt; Size: 1,057 bytes; and Date of Creation: Jun. 14, 2022) is herein incorporated by reference in its entirety.

BACKGROUND OF THE INVENTION

The present invention relates to a method of identifying effective antigen mixtures for tumor vaccines, a method of manufacturing tumor vaccines and to the tumor vaccine obtained.

Cancer is one of the most threatening diseases in humans, mainly because the prospects for successful treatment are low. One problem is that cancer summarizes a multitude of diseases with very different origin and development having only the occurrence of malignant tumors in common. It is by far not completely understood why and how one human develops tumors and others do not. Also the processes underlying successful treatment are not fully clarified.

While various proposals for treatment exists, the concept of activating the human patients own immune system seems one of the more promising approaches, since it is expected to result in less of the commonly severe side effects associated with the acknowledged treatments chemotherapy and radio therapy. Furthermore, the stimulated immune system should be more effective in eliminating residual tumor cells remaining in the patient's body after surgical removal of the primary tumor bearing the risk of disease recurrence and formation of metastases.

The immune system reacts to an encountered pathogen like a tumor cell with several steps. First a general unspecific action is initiated by cells like macrophages and dendritic cells which are present in all tissue and are activated by recognition of molecules shared by pathogens. Upon their activation they release inflammatory mediators which attract unspecific immune cells like phagocytes that in turn summon leukocytes and lymphocytes. A more specific reaction in response to pathogens that present antigens is the production of antibodies and specifc immune cells which are able to combat pathogens presenting the same antigen more rapidly upon a further encounter. Antigen(s) are defined as any substance which can be recognized specifically by components of the immune systems, e.g. B-cells (receptors and antibodies) and T-cells (T-cell receptor). Antigenicity means the property of a substance to be recognized by components of the immune system. Immunogenicity designates the property of a substance to induce an immune response, for which two things are required: the antigen plus the concurrent presence of a danger signal. An antibody is the result of the humoral immune response, present in serum, plasma, and in the interstitional fluid which recognizes the antigen and activates several effector mechanisms (e.g. ADCC=antibody dependend cellular cytotoxicity) for the elimination of the pathogen, e.g. a cancer cell. A danger signal is a substance such as pathogen-specific molecules (PAMPs, pathogen-associated molecular patterns) or endogenous host-derived signal released during cellular damage. According to theory signals of danger are sensed during innate and adaptive immune response and play an important role in discriminating self from nonself and in avoiding collateral damage in situations in which harmless nonself is present, see e.g. DOI: 10.1002/9780470015902.a0001210.pub2 and references cited therein. As a result of the cellular immune response, pathogen specific T-cells are present in the blood stream only. The specific T-cells recognize the pathogen, specifically tumor cells, via the antigens and activate effector mechanisms (e.g. cytotoxic T-cells).

One example for a treatment relying on activation of the immune system is treatment of renal cell carcinoma with a vaccine obtained from autologous tumor cells, designated RENIALET. As reported in Wittke et al. ("Rationales for a multi-epitope approach in autologous rean cell cancer tumor vaccine", J. Vaccines Vaccin 2016, ISSN: 2157-7560 JVV) efficacy could be shown in a phase III study (Jocham et al.: Adjuvant autologous renal tumour cell vaccine and risk of tumour progression in patients with renal-cell carcinoma after radical nephrectomy: phase III, randomised controlled trial. Lancet 2004; 363:594-99). However, it is anything but an easy task to obtain an approval for autologous vaccines. Every vaccine is made individually from tumor material obtained from the human patient by separating the tumor cells from the other tissue, inactivating the tumor cells and providing them in a form suitable for administration. The vaccine obtained is necessarily a very complex mix of cells and cell fragments which cannot be properly characterized. But exactly that is required for approval as medicament.

Thus, it would be desirable to find a method for providing more homogenous vaccines with well defined components. Due to the heterogeneity of tumors, even within one tumor from one human patient, this has not been achieved. Wittke et al. explicitly state that the "artificial composition of an individualized tumor vaccine seems to be impossible", see page 535, second sentence in the left column.

It was now surprisingly found that an effective vaccine can be assembled from synthetic antigens, when the relevant antigens for a specific type of tumor are determined for a set of at least 10 human patients by producing autologous vaccines according to the process applied for RENIALE™, application of this autologous vaccine to the human patients (for each patient the own autologous vaccine), isolation and determination of the antibodies and danger singnals produced by the human patients in response and assembly of the vaccine from all danger signals and antigens corresponding to the determined antibodies that have been found to be shared by at least 80% of the human patients.

SUMMARY OF THE INVENTION

Thus, the present invention solves the above object by a method of identifying an effective composition of antigens for a tumor vaccine (in short identification method), comprising the steps of determination of antibodies produced by at least 10 patients, preferably at least 20, more preferred at least 50 and most preferred at least 100 patients, after vaccination with an autologous vaccine obtained by gathering tumor material from the patients, separating the tumor cells from accompanying tissue, inactivating the tumor cells and providing them in a form suitable for administration as autologous vaccine, application of the autologous vaccine to the patients, isolation and determination of the antibodies produced by the patients that have been found to be shared by at least 80% of the patients, preferably by at least 50% and most preferred at least 30% of the patients, and identifying the antigens corresponding to the determined antibodies. The object is further solved by a method of manufacturing a tumor vaccine (in short manufacturing method), comprising identification of an effective composition of antigens with the identification method and assembling of the vaccine from the danger signals and synthetic antigens corresponding to the antigens identified with the identification method. Last but not least the object is solved by a tumor vaccine obtainable by the manufacturing method.

DETAILED DESCRIPTION OF THE INVENTION

The identification method is able to identify a set of antigens and danger signals suitable for manufacturing vaccines according to the manufacturing method without any need for autologous tumor material and its conversion into a vaccine. While effectivity of the vaccine according to the present invention increases with the number of patients included into the method of determining the effective antigens, it was found that 10 patients already provide a very good data base. Surprisingly, it was possible to determine a set of antigens that is shared by all tumors of a specific cancer type like renal cell cancer.

The identification method initially requires treating of a sufficient number human patients with an autologous vaccine. Further, the patients have to consent to donate blood or plasma or serum which is needed for determination of the antibodies produced in response to vaccination.

The treatment with autologous vaccines is state of the art, detailed descriptions can be found e.g. in EP 1 305 041 B1 and EP 1 974 742 A1 and numerous academic publications. The specific method of producing the autologous vaccine and treating the patients is not critical for the identification method according to the invention, the relevant features are use of an autologous vaccine and obtaining the blood, plasma or serum for determination of the specific immune response. The blood, plasma or serum should be donated approximately 3 to 12 months, preferably 5 to 8 months after vaccination.

Next, the antibodies (as surrogates for the specific T-cells) produced by the patients in response to autologous vaccination (with antigens plus danger signals) have to be isolated and determined. This is accomplished by standard procedures, for example test kits such as ELISA, Western blot, topological proteomics and FACS. Details are found e.g. in: Prikryl P, Vojtova L, Maixnerova D, Vokurka M, Neprasova M, Zima T, Tesar V. Physiol Res. 2017 Apr. 12. [Epub ahead of print]: Proteomics approach for identification of IgA nephropathy-related biomarkers in urine. Rapp C, Warta R, Stamova S, Nowrouzi A, Geisenberger C, Gal Z, Roesch S, Dettling S, Juenger S, Bucur M, Jungk C, DaoTrong P, Ahmadi R, Sahm F, Reuss D, Fermi V, Herpel E, Eckstein V, Grabe N, Schramm C, Weigand M A, Debus J, von Deimling A, Unterberg A, Abdollahi A, Beckhove P, Herold-Mende C. Acta Neuropathol. 2017 Mar. 22. doi: 10.1007/s00401-017-1702-1. [Epub ahead of print] Identification of T cell target antigens in glioblastoma stem-like cells using an integrated proteomics-based approach in patient specimens. Ramírez Rodríguez PB, Rosario Cruz R, Domínguez García DI, Hernández Gutiérrez R, Lagunes Quintanilla R E, Ortuño Sahagún D, González Castillo C, Gutiérrez Ortega A, Herrera Rodríguez SE, Vallejo Cardona A, Martínez Velázquez M. Exp Parasitol. 2016 November; 170:227-235. doi: 10.1016/j.exppara.2016.10.005. Epub 2016 Oct. 8.: Identification of immunogenic proteins from ovarian tissue and recognized in larval extracts of *Rhipicephalus (Boophilus) microplus*, through an immunoproteomic approach. Bassani-Sternberg M, Braunlein E, Klar R, Engleitner T, Sinitcyn P, Audehm S, Straub M, Weber J, Slotta-Huspenina J, Specht K, Martignoni M E, Werner A, Hein R, H Busch D, Peschel C, Rad R, Cox J, Mann M, Krackhardt A M. Nat Commun. 2016 Nov. 21; 7:13404. doi: 10.1038/ncomms13404. Direct identification of clinically relevant neoepitopes presented on native human melanoma tissue by mass spectrometry.

Once the antibodies have been isolated and determined, the relevant ones are selected by statistical analysis. It has been found that selecting those antibodies that are shared by 80% of the patients provides a set of antibodies that correspond to a set of antigens which is effective as vaccine. Preferably, antibodies that are shared by 50% of the patients, more preferred by 30% of the patients, are selected to provide more potent vaccines. It is noted that while selecting more antibodies the vaccine is more likely to contain enough antigens to stimulate the immune response against all tumor cells, the costs for the vaccine increase. So the selection is a compromise between completeness and costs.

The last step of the identification method according to the invention is the identification of the antigens corresponding to the selected anitbodies. This can be achieved easily with existing databases, e.g. Expasy (https://www.expasy.org) or by the combination of different methods like.

Affinity chromatography, HPLC, IEC, SEC and/or liquid chromatography in combination with different kinds of mass spectroscopy.

The use of gene-expression libraries (Protagen: http://protagen.com/tests/autoimmunebiomarkers. Here are more than 7000 human proteins expressed. They can be searched for the binding of specific (preferably) autoantibodies, in this case anti-tumor specific antibodies by classical solid phase assays (1. incubation of the antiserum with the solid phase bound antigen library, 2. Incubation with a labelled anti-species antibody, 3. Detection of the label [e.g., fluorometry, colorimetry, time resolve fluorimetry, etc]). It has to be kept in mind, that tumour immunity is always autoimmunity. The difference is the disease. In autoimmune diseases the autoantibody (or autoimmune reaction) is involved in the primary pathogenesis. In tumor patients, the autoimmunity against the tumor should become a part of the healing process.

Manufacturing of the tumor vaccine according to the invention relies on the antigens identified with the method according to the invention and enables to manufacture a vaccine which is effective against the type of tumor for which the antigens have been identified independent of the specific human patient. By pooling those antigens corresponding to antibody specificities that are found most often a set is obtained that reliably activates the immune system of any human patient against the tumor type. The vaccine is completed with danger signals known as such, see e.g. Chen W, Syldath U, Bellmann K, Burkart V, Kolb H. J Immunol. 1999 Mar. 15; 162 (6): 3212-9. Human 60-kDa heat-shock protein: a danger signal to the innate immune system. In particular, the danger signals are selected from the group consisting of HSP-27, HSP-47, HSP-60, HSP-70, HSP-72, HSP-90, HSP-105, HSP-110, multiple triacyl lipopeptides, glycolipids, lipopeptides, lipoproteins, lipoteichoic acid, zymosan-a Beta-glucan-, double-stranded RNA, poly I:C, lipopolysaccharide, fibrinogen, heparan sulfate and it's fragments, hyaluronic acid and it's fragments, nickel, Various opioid drugs, Bacterial flagellin, Profilin, diacyl lipopeptides, imidazoquinoline, loxoribine-a guanosine analogue-, bropirimine, single-stranded RNA, single-stranded Viral RNA, phagocytized bacterial RNA (24), unmethylated CpG Oligodeoxynucleotide DNA, bacterial ribosomal RNA sequence SEQ ID NO 1: CGGAAAGACC, urea, and any mixture of two or more of them, which are substances able to activate Toll-like receptors. Once the antibodies and therewith the antigens needed for a vaccine against a specific tumor type are identified, it is no longer necessary to gather tumor tissue and produce an autologous vaccine for a patient. A standard vaccine suitable for approval and for use in all human patients with the specific tumor type is obtained.

The synthetic antigens needed to assemble the vaccine are commercially available from companies like RD Systems, Wiesbaden-Nordenstadt, Germany, AbD serotec, Dusseldorf, Germany etc. If a specific antigen should not be available it can be expressed by known systems like the system presented from Protagen, for details see:

Wittke S, Baxmann S, Fahlenkamp D, Kiessig S T. Onco Targets Ther. 2016 Jan. 27; 9:523-37. doi: 10.2147/OTT.S92182. eCollection 2016. Tumor heterogeneity as a rationale for a multi-epitope approach in an autologous renal cell cancer tumor vaccine.

Knudsen E, Vail P, Balaji U, Ngo H, Botros I W, Makarov V, Riaz N, Balachandran V P, Leach S D, Thompson D M, Chan T A, Witkiewicz A K. Clin Cancer Res. 2017 Mar. 27. pii: clincanres.0162.2017. doi: 10.1158/1078-0432.CCR-17-0162. [Epub ahead of print] Stratification of Pancreatic Ductal Adenocarcinoma: Combinatorial Genetic, Stromal, and Immunological Markers.

Wafa El, Geary S M, Goodman J T, Narasimhan B, Salem A K. Acta Biomater. 2017 Mar. 1; 50:417-427. doi: 10.1016/j.actbio.2017.01.005. Epub 2017 Jan. 4. The effect of polyanhydride chemistry in particle-based cancer vaccines on the magnitude of the anti-tumor immune response.

Lokhov P G, Balashova E E. Recent Patents on Biotechnology, 2017, 11, 32-41. SANTAVAC™: A Novel Universal Antigen Composition for Developing Cancer Vaccines Lokhov P G, Balashova E E. J Immunol Res. 2016; 2016: 5031529. Allogeneic Antigen Composition for Preparing Universal Cancer Vaccines Andor N, et al.: Pan-cancer analysis of the extent and consequences of intra-tumor heterogeneity. Nat Med. 2016 January; 22 (1): 105-113.

In infections, tissue damage, tumor infiltrations microbial or tissue/cell components provide signals that alert the immune system to danger and promote the generation of immunity. In the absence of such signals, there is often no immune response or tolerance may develop. This has led to the concept that the immune system responds only to antigens perceived to be associated with a dangerous situation such as infection (Shi Y. et al.: Molecular identification of a danger signal that alerts the immune system to dying cells. Nature 425, 516-521 (2 Oct. 2003 doi: 10.1038/nature01991). Especially heat shock proteins (HSP) are identified as potent danger signals (Todryk S M et al.: Heat shock proteins refine the danger theory, Immunology. 2000 March; 99 (3): 334-337. doi: 10.1046/j.1365-2567.2000.00002.x). The antigen-chaperoning properties of HSP were highlighted in the tumor vaccination setting by the work of Srivastava (Srivastava P K, Menoret A, Basu S, Binder R J, McQuade K L. Heat shock proteins come of age: primitive functions acquire new roles in an adaptive world. Immunity. 1998; 8:657.). A number of HSP have now shown the ability to carry tumor antigens and generate protective immunity against live tumor challenge in murine models, including HSP-70, HSP-90 and gp96. In these experiments the HSP molecules were extracted and purified from tumors against which immunity was sought. HSP from normal tissues or HSP from tumors, which were then stripped of their associated peptides by adenosine triphosphatase (ATPase) before vaccination, did not confer protection against tumor (Udono H et al.: Cellular requirements for tumor-specific immunity elicited by heat shock proteins: tumor rejection antigen gp96 primes CD8+ T cells in vivo. Proc Natl Acad Sci USA. 1994; 9:3077. Suto R, Srivastava P K. A mechanism for the specific immunogenicity of heat shock-protein-chaperoned peptides. Science. 1995; 269:1585). According to the invention, such known danger signals are combined with the identified antigens in the vaccine.

The vaccine can contain adjuvants for enhancing the immune response in one preferred embodiment. Suitable are substances known as such, e.g. Al (OH) 3, oil-in-water emulsions, liposomes, tocopherol acetate, saponine, detox. LPS from salmonellae, ISCOMS (Immune stimulating complexes), CpG oligo nucleotides (bacterial DNA) and combinations thereof. Details on adjuvants can be found e.g. in https://www.capnetz.de/html/capnetz/events/sympo-sium2010/presentation/neue-adjuvantien-in-der-impfstof-fentwicklung-chancen-und-risiken.pdf.

Application of the vaccine for treatment of a human patient in need thereof is adjusted to need, i.e. predominantly depending on the specific tumor type, stage of the desease and patient response. Typically, vaccination starts one month after surgical removal of the tumor(s), and is continued by 1-12, e.g. 5 but also up to 24 additional vaccinations (usually 1-3 per month, preferably once monthly). A useful dosage can be, for example, $4\text{-}6 \times 10^6$ devitalized cells/mL. The vaccine according to the invention can be adapted for intramuscular (i.m.), intravenous (i.v.), intracutaneous (i.e.), intradermally (i.d.), or subcutaneous (s.c.) application to the patient. The preferred dosage form is i.d. vaccination.

The therapy of a specific human patient can be further optimized by analysing the tumor tissue, the blood (e.g. circulating tumor cells), plasma or serum of the patient after treatment with the vaccine according to the invention. Donation of blood, plasma or serum and isolation/determination of antibodies is carried out as for the identification method according to the invention. From the antibodies determined one can select additional tumor antigens corresponding to antibodies to individualize/adapt the vaccine composition. In that way a patient specific vaccine is obtained. Since the individual antigens and the danger signals can be subject of approval as such it is possible to establish a kit of approved danger signals and antigens for assembly of patient specific vaccines and individualization of the "standard" vaccine for a specific patient. Thereby, it is expected that total treatment costs and side effects can be reduced while effectivity is enhanced.

One major advantage of the identification method according to the invention and the optimization of the vaccine as described in the preceding paragraph is that they rely on the immune response in the human patient for identifying relevant antigens. Prior approaches had to rely on antibodies produced in laboratory animals, at best with a reconstituted human immune system. The optimization method relies on the human immune system of the patient to be treated. The method of identification relies on a set of human immune systems stimulated by autologous tumor antigens.

The method of identification according to the invention is suitable for all cancer diseases where a specific tumor type develops that can be used for manufacturing the autologous vaccine and provides a sufficient part of shared relevant antigens. Thus, it is expected that especially epithelial and non-epithelial tumors like pancreas cancer, colon cancer, Malignant melanoma, Prostate carcinoma, Non-small cell lung carcinoma, operable soft-tissue tumours, Glioblastoma multiforme and renal cell cancer can be treated with the vaccine obtained by assembly of danger signals and antigens identified according to the method of the invention.

The invention will be illustrated further with reference to the examples that follow, without restricting the scope to the specific embodiments described. If not otherwise specified any amount in % or parts is by weight and in the case of doubt referring to the total weight of the composition/mixture concerned.

The invention further includes all combinations of described and especially of preferred features that do not exclude each other. A characterization as "approximately", "around" and similar expression in relation to a numerical value means that up to 10% higher and lower values are included, preferably up to 5% higher and lower values, and in any case at least up to 1% higher and lower values, the exact value being the most preferred value or limit.

The term "substantially free" means that a particular material is not purposefully added to a composition, and is only present in trace amounts or as an impurity. As used herein, unless indicated otherwise, the term "free from" means that a compositin does not comprise a particular material, i.e. the compostion comprises 0 weight percent of such material.

Example 1: Method of Identification

Tumor material was received from 133 human patients who underwent radical nephrectomy, donating the material on a voluntary base. All patients gave informed consent. The tumor material (about 1 g) was placed in sterile RMPI 1640 transport medium (Invitrogen; Karlsruhe, Germany) and shipped at 2-8° C. within 24 h to the central laboratory. The median age of patients at primary diagnosis is 60 years and the male to female ratio is 2 to 1.

Preparation of the tumor cell lysate (TCL) started with removal of macroscopically visible non-tumor tissue. In order to obtain a single cell suspension, the remaining tumor tissue was cut into small pieces (~1 mm$^3$) and then passed through a sieve with a defined grid size (50 mesh). Cells are purified by Percoll density gradient centrifugation. Subsequently, the cells were incubated with interferon-γ and α-tocopherol acetate. The tumor cell suspension was aliquoted in single doses of 1 mL. Threefold rapid freezing at −82±5° C. and thawing was used to devitalize the cells.

For detection of antigens ELISA test kits were used. Sample dilutions were adjusted according to pre-experiments. Free hemoglobin (fHb) was measured to make sure, that no contamination from residual red blood cells of residual plasma influenced the results.

The concentrations of the danger signals HSP-60 and HSP-70 were detected by ELISA test kits. SDS-PAGE and Western Blotting were carried out according to standard procedures in 4-20% gradient mini-gels (SERVA, Heidelberg, Germany) utilizing a molecular weight marker (Bio-Rad, Hercules, CA, USA). Protein bands were insolubilized onto PVDF-membrane. Incubations with primary or secondary antibodies/protein-A-HRP were done in TBS 0.1% Tween 20, 1% w/v BSA. The substrate reaction (insoluble TMB+$H_2O_2$) [Seramun, Wolzig, Germany] was carried out for 20 min. The reaction was stopped by substrate removal (washing). Statistical analysis was carried out by descriptive methods using Microsoft Excel. Topological proteomics to demonstrate the heterogeneity of tumor tissue and cell suspensions were performed.

The results can be summarized as follows: There is a huge antigenic heterogeneity between the patients tumors. The antigenic composition of the tumors is highly individual on the found antigen pattern and concentrations. A few antigens are present on most tumors: TPS (Tissue polypeptide specific antigen [van Poppel H et al.: Serum tissue polypeptide antigen (TPA) as tumor marker for bladder cancer. Anticancer Res. 1996 July-August; 16 (4B): 2205-7.]), TPA (Tissue polypeptide antigen [Weber K.: Tissue polypeptide antigen (TPA) is related to the non-epidermal keratins 8, 18 and 19 typical of simple and non-squamous epithelia: re-evaluation of a human tumor marker. EMBO J. 1984 November; 3 (11): 2707-2714.]), NSE (Neurone specific enolase [Lorenz J et al.: Neuron-specific enolase (NSE) and squamous cell carcinoma antigen (SCC) as serum markers in the diagnosis of bronchial carcinoma. Pneumologie. 1990 November; 44 (11): 1259-63.], CA-IX (carbonic anhydrase IX [Lam J S, Pantuck A J, Belldegrun A S, Figlin R A. G250: a carbonic anhydrase IX monoclonal antibody. Curr Oncol Rep. 2005; 7:109-115. Said J. Biomarker discovery in urogenital cancer. Biomarkers. 2005; 10 Suppl 1: S83-S86.], and CYFRA (CYFRA 21-1 is a fragment of cytokeratin 19 [Cytokeratin Fragment] [Pujol J L et al.: CYFRA 21-1: a new marker of epidermoid cancer of the bronchi. Comparison with 3 other markers. Presse Med. 1993 Jun. 19; 22 (22): 1039-42.]) are present in most tumors (>90%), in composition with at least 2 of this 5 in 100% of all RCC. TPA, TOPA and CYFRA are cytokeratins, which are represented by a peptide with a sequence present in all three antigens: Peptide sequence: SEQ ID NO. 2: QRGELAIKDANAKLSELEAALQRAKQ (Johansson A, Sandström P, Ullén A, et al. Epitope specificity of the monoclonal anticytokeratin antibody TS1. Cancer Res. 1999; 59 (1): 48-51.). This peptide can be used for solid phase coating either for analytical techniques to detect specific antibodies against cytokeratins or as well for the affinity chromatographic purification of human antibodies of antibody expression systems like phage libraries.

The last step of the identification method according to the invention is the identification of the antigens recognized by the antibodies induced by the tumor vaccine. For this the gene-expression library Protagen: http://protagen.com/tests/autoimmunebiomarkers is used. The more than 7000 human proteins expressed are searched for the binding of the identified antibodies. Slides containing this spotted library are incubated with the patients serum (preferably serum drawn 4 weeks after the last vaccination with the tumor vaccine) at a dilution of 1:50 in PBS, 0.1% v/v Tween 20 (PBST) for 45 min. The slides are washed 3 times in (PBST) and now incubated with a fluorescence labelled anti-human-lgG for another 45 min (concentration: 1 μg/mL in PBST) before the slides are again washed 3 times in PBST. The evaluation is carried out by a fluorescence scan. Recognized antigens appear fluorescent.

Example 2: Vaccine

For manufacturing a vaccine, the identified antigens are either obtained commercially or made in a known manner, adjusted to $10^6$ cells/mL and combined with the danger signals HSP-60 and/or HSP-70 in a concentration of 3 ng/ml up to 1000 µg/mL in cell NaCl/Glucose medium. The solution is filled into 1 mL sterile vials and can be stored below −40° C. until use. The vaccine can be used for the vaccination of patients. The composition of the vaccine can be done based on the statistical evaluation of the most present antigens or on an individual level, based on the preexisting anti-tumor response to get those patients boostered against their tumor.

Some of the treated human patients already show an immune response to their tumor. This existing immune response can be evaluated analogously to example 1. In those cases the vaccine composition is adjusted according to the antigen pattern recognized by the patients immune system.

It is contemplated that the method of identification and the methods of making vaccines can be applied to non-human mammals analogously.

The invention claimed is:

1. A method of manufacturing a tumor vaccine comprising the steps of:
   vaccinating at least 10 human patients with autologous tumor cell lysate;
   isolating antibodies induced by the autologous tumor cell lysate;
   identifying antigens bound by the isolated antibodies;
   selecting identified antigens shared by at least 80% of the human patients; and
   assembling a tumor vaccine comprising the selected antigens and danger signals.

2. The method according to claim 1 further comprising the selecting of identified antigens shared by at least 50% of the human patients and assembling the tumor vaccine including said antigens.

3. The method according to claim 1 wherein the at least 10 human patients are at least 50 human patients.

4. The method according to claim 1, wherein the tumor is of epithelial or endothelial or mesothelial origin or a leukemia.

5. The method according to claim 1, wherein the danger signals are selected from the group consisting of HSP-27, HSP-47, HSP-60, HSP-70, HSP-72, HSP-90, HSP-105, HSP-110, multiple triacyl lipopeptides, glycolipids, lipopeptides, lipoproteins, lipoteichoic acid, zymosan, double-stranded RNA, poly I:C, lipopolysaccharide, fibrinogen, heparan sulfate, heparan sulfate fragments, hyaluronic acid, hyaluronic acid fragments, nickel, opioid drugs, Bacterial flagellin, Profilin, diacyl lipopeptides, imidazoquinoline, loxoribine, bropirimine, single-stranded RNA, single-stranded Viral RNA, bacterial RNA in a phagocyte, unmethylated CpG Oligodeoxynucleotide DNA, bacterial ribosomal RNA sequence SEQ ID NO 1: CGGAAAGACC, urea, a mixture of two or more thereof.

6. The method according to claim 1, wherein the tumor vaccine is assembled from antigens chosen from synthetic antigens, recombinant antigens, antigens of natural origin, peptides, proteins, glycans, branched polysaccharides and mixtures of two or more of those.

7. The method of claim 1 further comprising adding adjuvants to the assembled tumor vaccine, wherein the adjuvants are selected from the group consisting of Al(OH)

3, aluminum salts, oil-in-water emulsions, liposomes, tocopherol acetate, saponine, detoxified LPS from Salmonellae, CpG oligo nucleotides and combinations thereof.

8. The method according to claim 1, wherein tumor tissue, blood, plasma or serum of a patient is analyzed after treatment with the assembled tumor vaccine to isolate additional antibodies and identify additional antigens for addition to the assembled tumor vaccine.

9. The method according to claim 1 further comprising the selecting of identified antigens shared by at least 30% of the human patients and assembling the tumor vaccine including said antigens.

10. The method according to claim 1 wherein the at least 10 human patients are at least 100 human patients.

11. The method according to claim 10 further comprising the selecting of identified antigens shared by at least 30% of the human patients and assembling the tumor vaccine including said antigens.

12. The method according to claim 1, wherein the vaccine is manufactured to effective against tumors caused by one of the following: pancreatic cancer, colon cancer, Malignant melanoma, Prostate carcinoma, Non-small cell lung carcinoma, operable soft-tissue tumors, Glioblastoma multiforme and renal cell cancer.

* * * * *

SEQUENCE LISTING

```
<160> NUMBER OF SEQ ID NOS: 2

<210> SEQ ID NO 1
<211> LENGTH: 10
<212> TYPE: RNA
<213> ORGANISM: unknown
<220> FEATURE:
<223> OTHER INFORMATION: bacterial ribosomal

<400> SEQUENCE: 1
cggaaagacc                                                          10

<210> SEQ ID NO 2
<211> LENGTH: 26
<212> TYPE: PRT
<213> ORGANISM: Unknown
<220> FEATURE:
<223> OTHER INFORMATION: TPA, TOPA CYFRA
<300> PUBLICATION INFORMATION:
<301> AUTHORS: Johansson A, Sandstrom P, Ullen A, et al.
<302> TITLE: Epitope specificity of the monoclonal anticytokeratin
      antibody TS1
<303> JOURNAL: Cancer Res.
<304> VOLUME: 59
<305> ISSUE: 1
<306> PAGES: 48-51
<307> DATE: 1999

<400> SEQUENCE: 2

Gln Arg Gly Glu Leu Ala Ile Lys Asp Ala Asn Ala Lys Leu Ser Glu
1               5                   10                  15

Leu Glu Ala Ala Leu Gln Arg Ala Lys Gln
            20                  25
```